United States Patent [19]

Sarnoff et al.

[11] Patent Number: 4,689,042
[45] Date of Patent: Aug. 25, 1987

[54] AUTOMATIC MEDICAMENT INGREDIENT MIXING AND INJECTING APPARATUS

[75] Inventors: Stanley J. Sarnoff; William R. Tarello, both of Bethesda; Claudio Lopez, Silver Spring, all of Md.; Daniel W. Karcher, Great Falls, Va.

[73] Assignee: Survival Technology, Inc., Bethesda, Md.

[21] Appl. No.: 735,995

[22] Filed: May 20, 1985

[51] Int. Cl.$^4$ .............................................. A61M 5/00
[52] U.S. Cl. .................................... 604/89; 604/136; 604/191
[58] Field of Search ...................... 604/82, 87, 88, 89, 604/90, 91, 135, 136, 139, 148, 157, 85, 86, 92

[56] References Cited

U.S. PATENT DOCUMENTS

| | | |
|---|---|---|
| 2,459,875 | 1/1949 | Folkman ............................... 604/90 |
| 2,591,046 | 4/1952 | Brown . |
| 3,326,215 | 6/1967 | Sarnoff et al. . |
| 3,451,393 | 6/1969 | Sarnoff . |
| 3,464,412 | 9/1969 | Schwartz . |
| 3,494,359 | 2/1970 | Zackheim . |
| 4,059,109 | 11/1977 | Tischlinger . |
| 4,178,928 | 12/1979 | Tischlinger ........................ 604/139 |
| 4,214,584 | 7/1980 | Smirnov et al. .................... 604/139 |
| 4,226,235 | 10/1980 | Sarnoff et al. . |
| 4,226,236 | 10/1980 | Genese . |
| 4,258,713 | 3/1981 | Wardlaw ............................. 604/139 |
| 4,329,988 | 5/1982 | Sarnoff et al. . |
| 4,394,863 | 7/1983 | Bartner . |
| 4,405,317 | 9/1983 | Case . |

FOREIGN PATENT DOCUMENTS 0554034 3/1958 Canada ................................ 604/139
2657053 6/1977 Fed. Rep. of Germany ...... 604/157

Primary Examiner—Stephen C. Pellegrino
Attorney, Agent, or Firm—Cushman, Darby & Cushman

[57] ABSTRACT

An automatic injector apparatus comprising an outer housing assembly, a hypodermic needle, first and second containers, a first liquid medicament ingredient in the first container and a second medicament ingredient in the second container, first and second pistons in the first and second containers respectively, a releasable stressed spring arrangement capable of being released twice, once for movement through a first piston moving stroke and second through a second piston moving stroke, a first releasing device operable in response to a first predetermined actuating procedure for accomplishing a first release of the spring arrangement so as to effect movement of the first piston through a liquid medicament ingredient moving stroke causing the liquid medicament ingredient to mix with the medicament ingredient in the second container to form liquid medicament and a second releasing device operable in response to a second actuating procedure for accomplishing a second release of the spring arrangement so as to effect movement of the second piston through an operative stroke causing the hypodermic needle to be moved into the muscle tissue of the patient and the liquid medicament to be moved through the needle into the muscle tissue of the patient.

34 Claims, 13 Drawing Figures

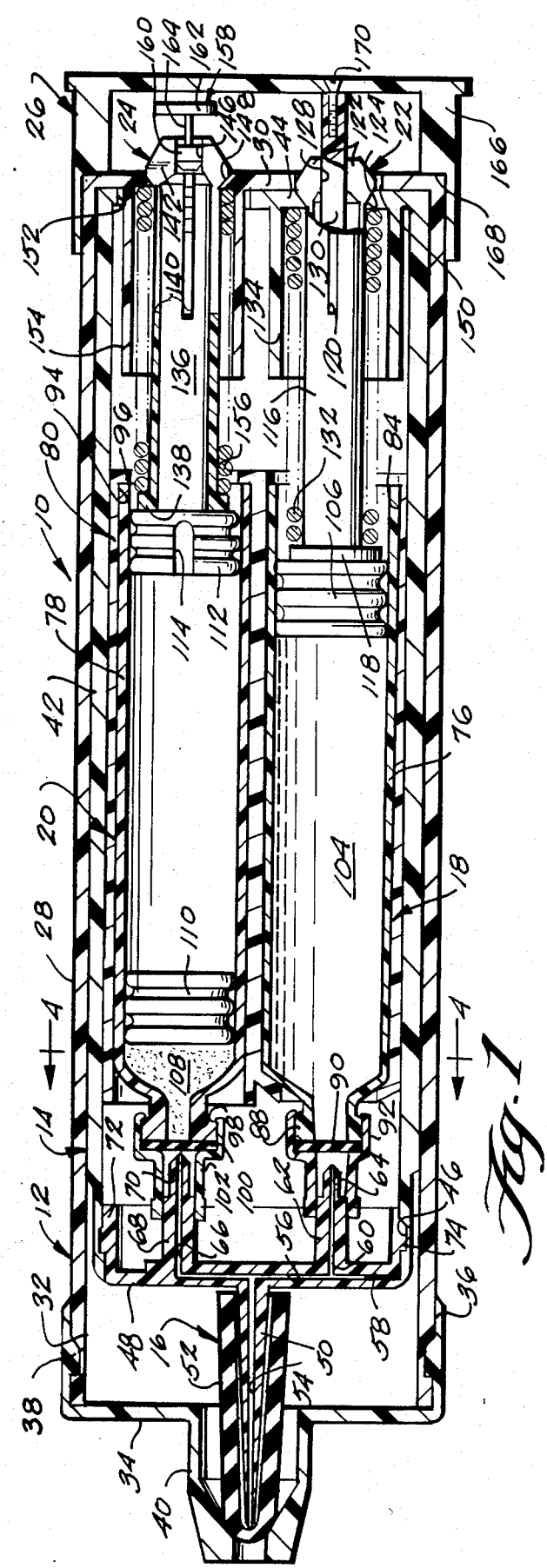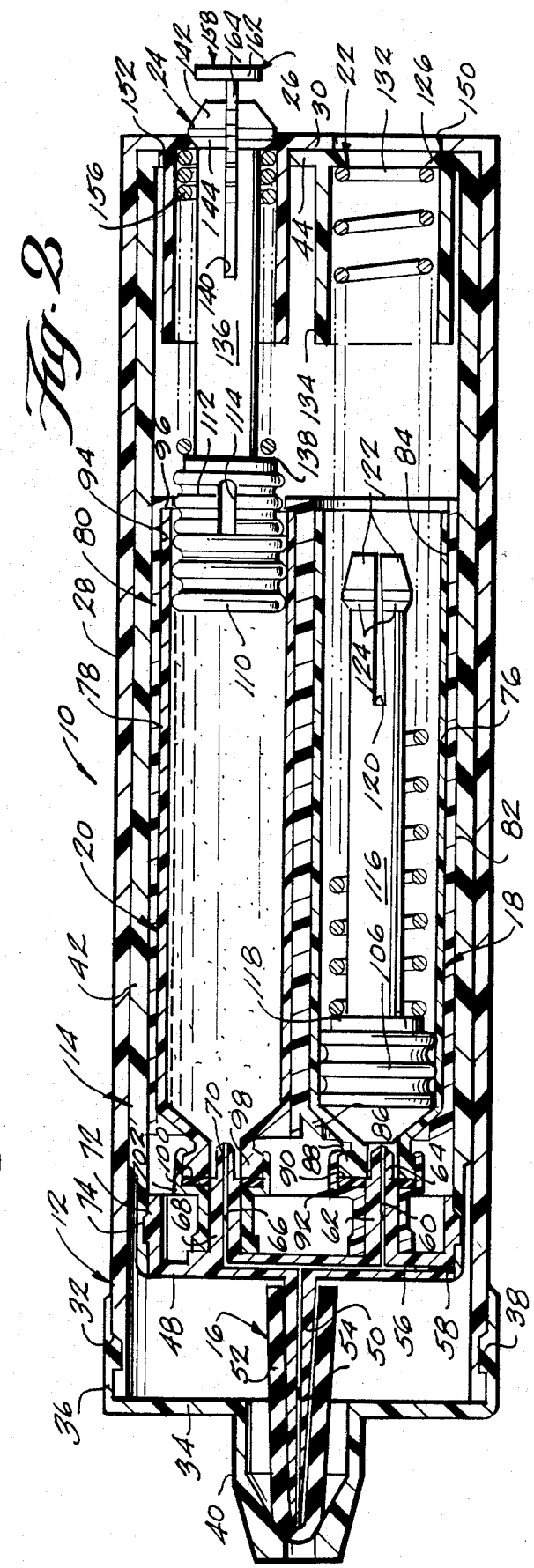

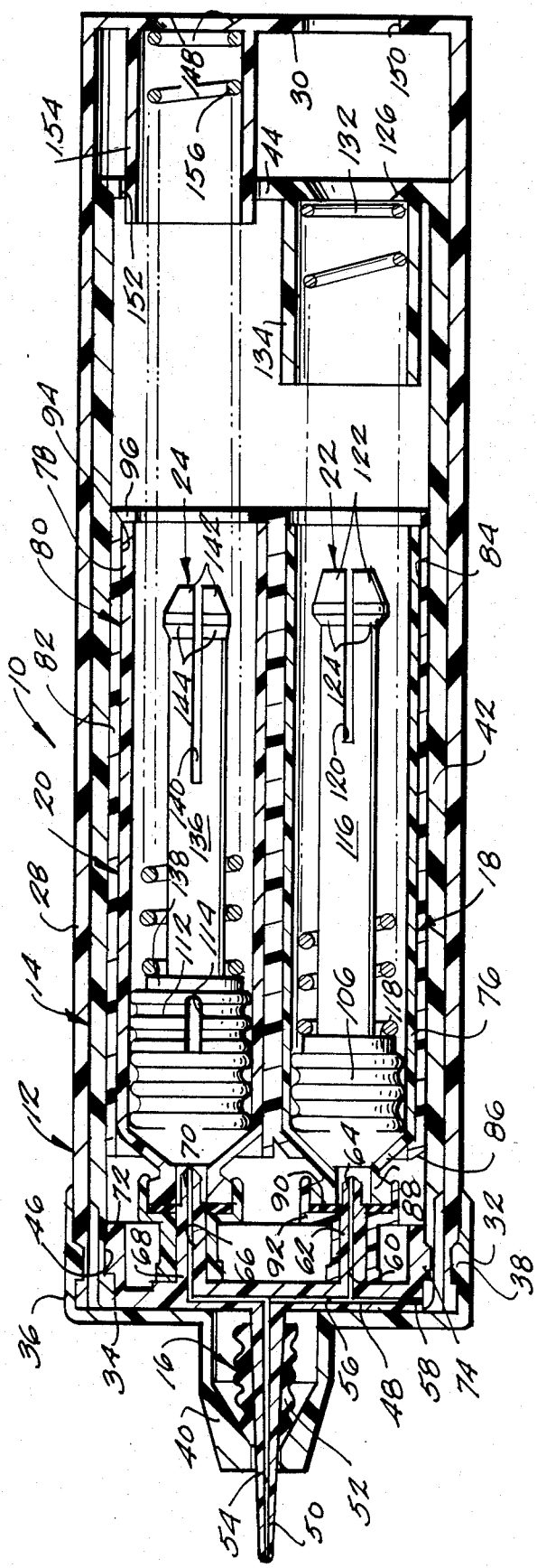
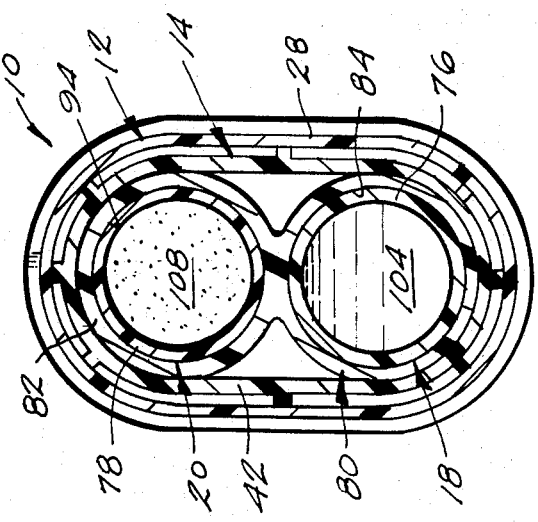

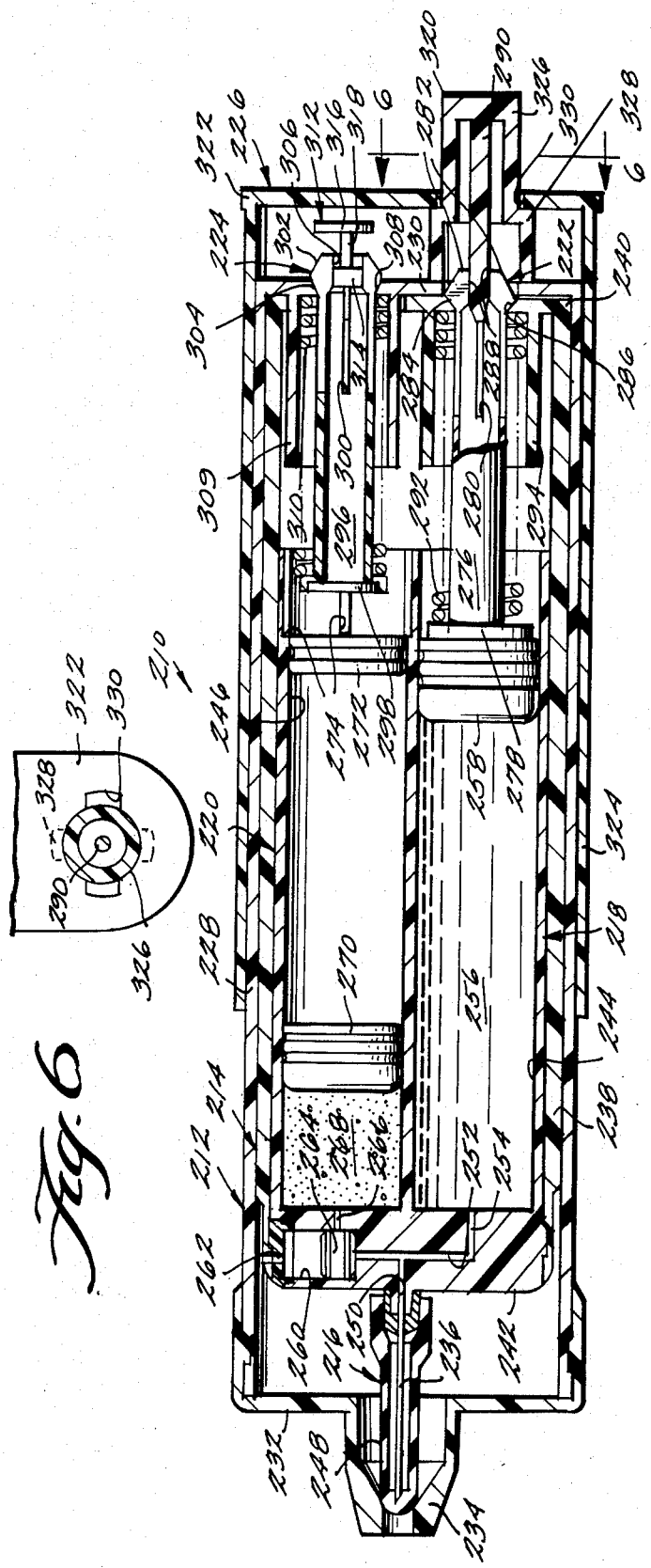

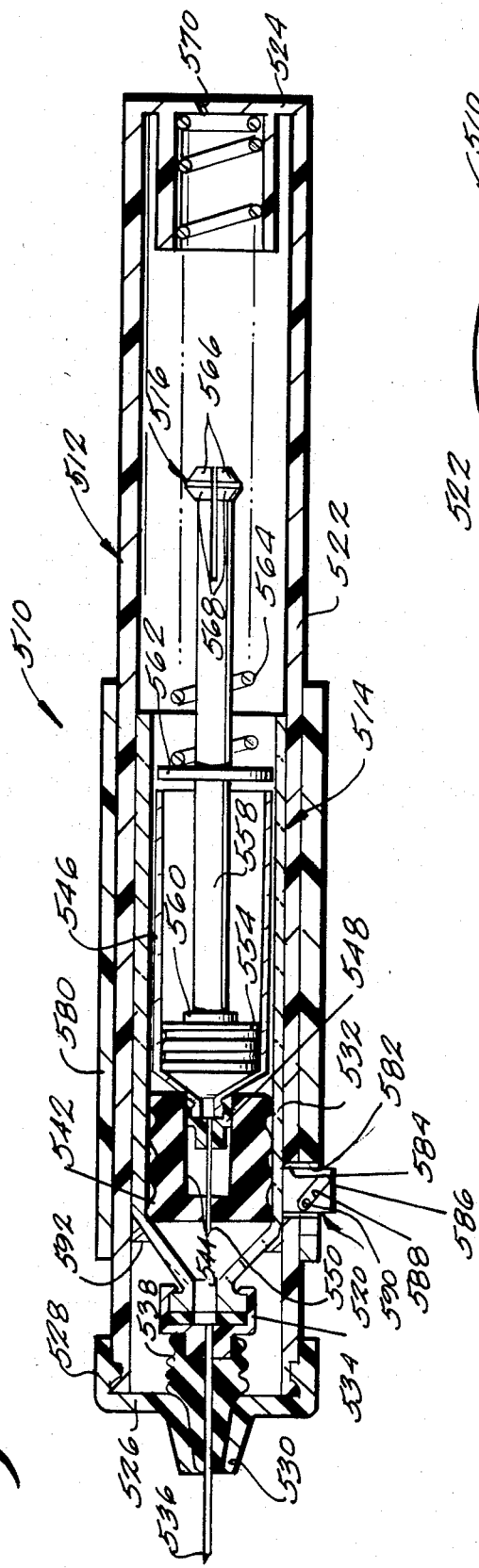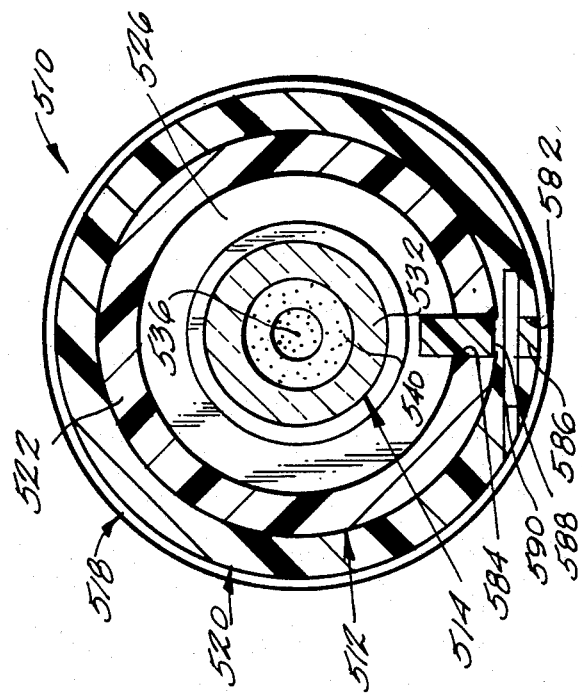

AUTOMATIC MEDICAMENT INGREDIENT MIXING AND INJECTING APPARATUS

This invention relates to automatic injectors and more particularly to automatic injectors of the type operated by the release of a stressed spring assembly.

Spring operated automatic injectors have been known for many years. The most extensive use of automatic injectors of this type has been to contain a chemical warfare antidote. Other uses of injectors of this type include antidotes for bee stings and anti-arrhythmic medicaments, such as lidocaine. In recent years there have been proposed multi-dosage automatic injectors. Such multi-dosage automatic injectors include the packaging of two single dose injectors in one package, U.S. Pat. No. 4,329,988 or providing a single device with a single actuating mechanism with plural medicament cartridges, U.S. Pat. No. 4,226,235. Where the plural medicaments are in liquid form they can be packaged in a single medicament cartridge assembly for sequential injection by spring actuation, see U.S. Pat. No. 4,394,863.

A problem with respect to the single cartridge type units is that the amount of liquid medicament that can be utilized is severely limited. A disadvantage of the dual cartridge units is that they become quite bulky and more difficult to handle. This is particularly true where fairly large amounts of liquid medicament must be injected.

The present invention is based upon the fundamental principal that these two disadvantages of the prior art can best be accomodated by the provision of an automatic injector assembly which in its storage condition contains the medicament ingredients, at least one of which is in liquid form and then utilizing the automatic spring function provided to mix the medicament ingredients to form liquid medicament and then to inject the liquid medicament.

The patented prior art contains disclosures of many manually operable syringes capable of containing a plurality of separate medicament ingredients and of subsequently mixing and injecting the same. Examples of prior art of this type include U.S. Pat. Nos. 2,591,046, 3,326,215, 3,464,412, 3,494,359, 4,059,109, 4,226,236, and 4,405,317.

While mixing type syringes have been known in the prior art for many years, applicant is unaware of any automatic spring actuated type injectors having the capability of first mixing a plurality of separately contained medicament ingredients and subsequently injecting the same. In commonly assigned U.S. Pat. No. 3,451,393 there is disclosed an automatic infusion device which includes a housing for receiving a pair of side by side containers each of which contains a separate medicament ingredient. Stressed spring assemblies are associated with each of the two containers, one of which is releasable to accomplish the mixing procedure and the release of the other of which serves to pressurize the mixture for use in the infusion process.

In view of the above, it is an object of the present invention to provide an automatic injector device of the spring actuated type which has the capability of first mixing a plurality of separately contained medicament ingredients and then effecting an automatic injection thereof into the muscle tissue of a patient. This capability is highly desirable since it accomplishes under emergency conditions an intramuscular injection of a maximum amount of medicament in liquid form for absorption into the blood so as to accomplish a desired therapeutic effect.

In accordance with the principles of the present invention, the above object is accomplished by providing an automatic injector apparatus comprising an outer housing assembly, a hypodermic needle, first and second containers, a first liquid medicament ingredient in the first container and a second medicament ingredient in the second container, first and second pistons in the first and second containers respectively, a releasable stressed spring arrangement capable of being released twice, once for movement through a first piston moving stroke and second through a second piston moving stroke, a first releasing device operable in response to a first predetermined actuating procedure for accomplishing a first release of the spring arrangement so as to effect movement of the first piston through a liquid medicament ingredient moving stroke causing the liquid medicament ingredient to mix with the medicament ingredient in the second container to form liquid medicament and a second releasing device operable in response to a second actuating procedure for accomplishing a second release of the spring arrangement so as to effect movement of the second piston through an operative stroke causing the hypodermic needle to be moved into the muscle tissue of the patient and the liquid medicament to be moved through the needle into the muscle tissue of the patient.

Another object of the present invention is the provision of an automatic injector or injecting apparatus capable of mixing a contained liquid medicament ingredient and another medicament ingredient to form liquid medicament and of subsequently injecting the liquid medicament, which apparatus is simple in construction, effective in operation and economical to manufacutre.

These and other objects of the present invention will become more apparent during the course of the following detailed description and appended claims.

The invention may best be understood with reference to the accompanying drawings wherein illustrative embodiments are shown.

In the drawings

FIG. 1 is a longitudinal sectional view of an automatic mixing and injecting apparatus embodying the principles of the present invention showing the parts in their storage position;

FIG. 2 is a view similar to FIG. 1 showing the parts in their mixing or liquid medicamant forming position;

FIG. 3 is a view similar to FIG. 1 showing the parts in their final injecting position;

FIG. 4 is a sectional view taken along the line 4—4 of FIG. 1;

FIG. 5 is a view similar to FIG. 1 of another form of automatic mixing and injecting apparatus embodying the principles of the present invention;

FIG. 6 is a sectional view taken along the lines 6—6 of FIG. 5;

FIG. 12 is a view similar to FIG. 3 of the apparatus shown in FIG. 10, and

FIG. 13 is a sectional view taken along the lines 13—13 of FIG. 10.

Figure 7:
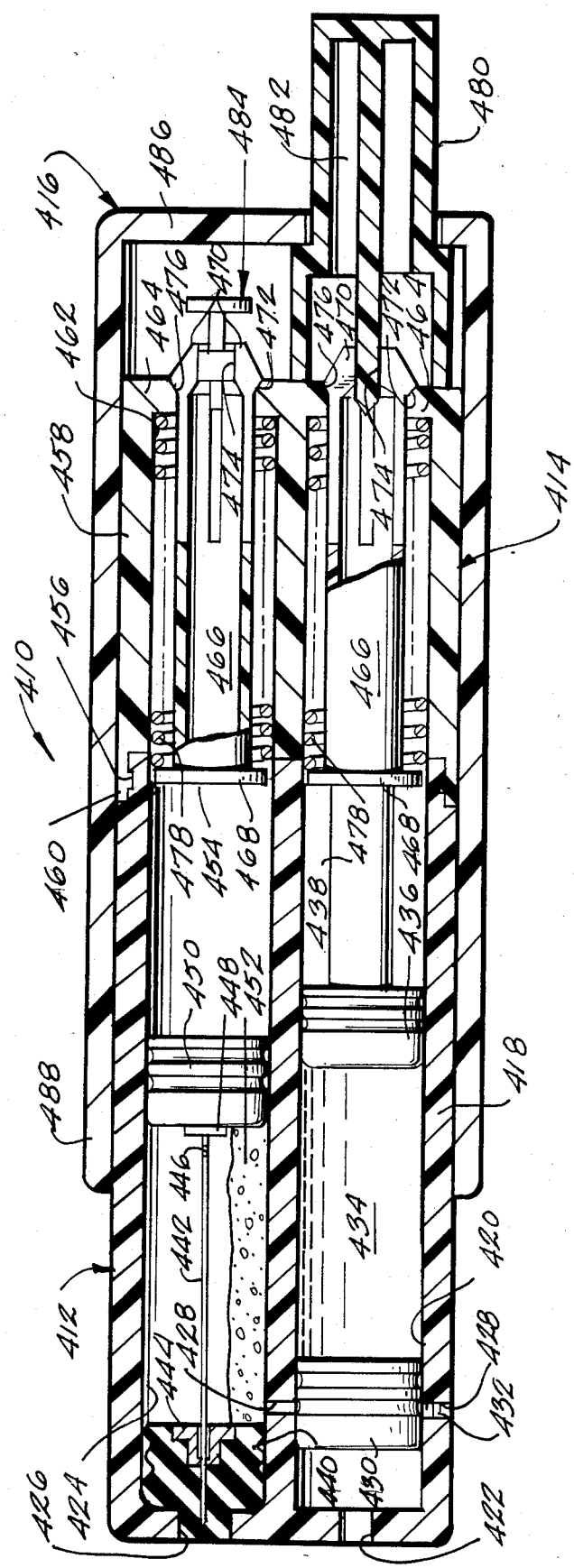
FIG. 7 is view similar to FIG. 1 of still another form of automatic mixing and injecting apparatus embodying the principles of the present invention.

Referring now more particularly to the drawings, there is shown in FIG. 1 an automatic injector or mixing and injecting apparatus, generally indicated at 10, which embodies the principles of the present invention. As shown, the apparatus 10 includes an outer housing assembly 12 having an inner housing structure 14 mounted therein for rectilinear sliding movement from a storage position, as shown in FIG. 1, forwardly into an injecting position, as shown in FIG. 3. Inner housing structure 14 has connected thereto a hypodermic needle assembly 16. A first liquid medicament ingredient container assembly 18 is operatively associated with the inner housing structure 14 and a side by side related second medicament ingredient container assembly 20 is likewise operatively associated with the inner housing structure 14. Operatively associated with the first and second container assemblies 18 and 20 are first and second stressed spring assemblies 22 and 24. The first stressed spring assembly 22 is mounted in a stressed condition on the inner housing structure 14 in operative relation with the first container assembly 18. The second stressed spring assembly 24 is connected with the outer housing assembly 12 in a stressed condition in operative relation with the second container assembly 20. A safety cap and releasing pin assembly 26 is mounted in operative relation with respect to the first and second spring assemblies 22 and 24 for rendering the apparatus inoperable and for enabling the first spring assembly to be released in response to a first predetermined actuating procedure and the second spring assembly to be released in response to a second actuating procedure.

As shown, the outer housing assembly 12 includes an elongated tubular housing member 28 having an integral rear wall 30 and an open forward end which has formed in the exterior periphery thereof an annular groove 32. A forward housing member 34 includes a rearward annular skirt 36 having an annular ridge 38 formed on the interior periphery thereof for cooperatively engaging within the annular groove 32 so as to secure the two housing members together. As shown, the housing member 34 also includes a forwardly projecting centrally apertured skin contacting portion 40.

The inner housing structure 14 includes a tubular member 42 having a ribbed exterior periphery which slidably engages the interior periphery of the outer housing member 28. The inner housing member 42 also includes a rear wall 44 and, like the outer housing member 28, its forward end is open and has an annular groove 46 formed therein. This time the annular groove 46 is on the interior surface of the inner housing member 42 rather than the outer surface thereof as with the outer housing member 28. Fixedly mounted within the open forward end of the inner housing member 42 is a forward inner housing member 48.

As shown, the inner housing member 48 includes an integral needle element 50 extending forwardly from the central portion thereof which constitutes part of the hypodermic needle assembly 16. The needle assembly 16 also includes a resilient sheath 52 the forward end of which engages within the central opening in the skin engaging portion 40 of the outer housing assembly 12. The tip of the resilient sheath 52 closes the forward central aperture of the outer housing assembly 12 and seals the sharp piercing end of the needle element 50. The needle element 50 is of the hypodermic type including an interior passage 54 for the conveyance of a liquid medicament outwardly thereof into the muscle tissue of the patient. The rearward end of the needle passage 54 connects with a cross passage 56 formed in the forward inner housing member 48. As shown, one end of the cross passage 56 is plugged, as indicated at 58, and at a position spaced from the plug, the cross passage 56 communicates with a first rearwardly extending passage 60 which is formed in a first rearwardly projecting cylindrical portion 62 having a rearwardly extending diaphragm piercing element 64 integral therewith. The opposite end of the cross passage 56 connects with a second rearwardly extending passage 66 formed in a second rearwardly extending cylindrical portion 68 which terminates in a diaphragm piercing element 70. It will be noted that the member 48 includes in addition a rearwardly extending peripheral skirt 72 having an exterior annular ridge 74 thereon which is adapted to cooperate with the annular groove 46 to secure the forward inner housing member 48 with the tubular inner housing member 42.

The first and second container assemblies 18 and 20 include first and second containers 76 and 78 which, as shown, are formed of plastic material although they may be formed of glass if desired. The first and second containers 76 and 78 are arranged to engage within a container support structure, generally indicated at 80. The container support structure 80 includes a peripheral wall 82 which includes exterior surfaces which engage with the interior periphery of the inner housing member 42 for sliding movement with respect thereto from a storage position, as shown in FIG. 1, to a mixing or liquid medicament forming postion, as shown in FIG. 2. The container support structure 80 includes a first bore 84 which extends forwardly from the rearward end thereof and terminates in an annular shoulder 86 so as to receive the first container 76 forwardly therein. The first container is formed by a cylindrical wall which is open at its rearward end and which has an exteriorly flanged necked down forward end, indicated at 88. A piercable diaphragm 90 is mounted on the forward end of the exteriorly flanged necked down end 88 and is retained thereon by a hub assembly 92 which includes a rearward portion extending over the exterior annular flange of the container and a forward portion of reduced diameter which slidably sealingly engages the associated rearwardly projecting cylindrical portion 62 of the inner housing member 48.

The container support structure 80 also includes a second cylindrical bore 94 which extends rearwardly from the forward end thereof and terminates in a rearward inwardly directed annular shoulder 96 so as to receive the second container 78 rearwardly therein. The second container 78 is similar to the first and includes an open rear end and an exteriorly flanged necked down open forward end 98 which is closed by a piercable diaphragm 100 retained thereon by hub assembly 102 having a rearward portion fixed to the exterior flange and a forward portion of reduced diameter slidably sealingly engaging the associated rearwardly extending cylindrical portion 68.

Mounted within the first container 76 is a liquid medicament ingredient 104 which is sealed at its forward end by the associated piercable diaphragm and at its rearward end by a piston 106 formed of resilient material which is slidably sealingly mounted within the rearward interior end portion of the container 76.

Similarly, the second container 78 has mounted therein a medicament ingredient 108 which, as shown, is in dry form and more specifically a freeze dried powder. Here again, the forward end of the medicament ingredient 108 is sealed by the associated diaphragm 100 and its rearward end is sealed by a piston 110 which is constructed similarly to the piston 106 previously described. Since, as shown, the second piston 110 is disposed near the forward end portion of the second container 78 in its storage condition, the remaining portion of the second container disposed rearwardly of the piston 110 desirably should be maintained in a sterile condition since it is to receive liquid medicament when the second piston 110 is moved rearwardly from its storage position to a position enabling the liquid medicament to be moved forwardly. In order to seal the rearward end of the second container 78 there is mounted therein a sealing piston 112 which has venting slots 114 formed in the forward portion thereof.

The first stressed spring assembly 22 includes a hollow plunger 116 the forward end of which is flanged, as indicated at 118, and disposed in engagement with the first piston 106 forming a part of the first container assembly 18. The rearward portion of the plunger 116 is slotted, as indicated at 120, to form a plurality of annularly spaced resilient fingers 122 which are integral with the plunger. The fingers 122 are formed with exterior plunger retaining surfaces 124 which face forwardly and outwardly and extend at an angle of approximately 45°. It will be noted that the rearward end wall 44 of the inner housing member 42 is apertured to receive the plunger and is provided with cooperating interior plunger retaining surfaces 126 which face inwardly and rearwardly and extend at an angle of approximately 45°. The fingers 122 of the plunger 116 are also provided with a series of interior plunger releasing surfaces 128. These surfaces are disposed within a common cylindrical plane which has a diameter substantially less than the interior diameter of the hollow plunger. The interior plunger releasing surfaces extend from the rearward end of the fingers inwardly a short distance. Mounted within the interior plunger releasing surfaces 128 of the fingers 122 is a first releasing pin 130 which, as shown, forms a part of the safety cap and releasing assembly 26.

It will be understood that when the releasing pin 130 is disposed in engagement with the interior plunger releasing surfaces 128 the associated fingers 122 are prevented from being deflected radially inwardly. The releasing pin 130 thus serves to insure that the exterior plunger retaining surfaces 124 of the fingers 122 will be maintained in engagement with the cooperating plunger retaining surfaces 126 of the inner housing structure 14. This maintenance is provided notwithstanding the bias which is present by virtue of a stressed coil spring 132 forming a part of the spring assembly 22. Coil spring 132 is mounted over exterior periphery of the plunger 116 with its forward end in engagement with the flange 118 and its rearward end in engagement with the forwardly facing surface of the rearward end wall 44 of the inner housing structure 14. In order to center the coil spring 132, preferably the end wall 44 is provided with an integral forwardly extending cylindrical skirt portion 134 which surrounds the rearward end portion of the coil spring 132.

The second stressed spring assembly 24 is similar to the first in that it includes a hollow plunger 136 having a flange 138 on the forward exterior periphery thereof and slots 140 formed in the rearward end portion thereof so as to define a series of annularly spaced radially inwardly deflectable spring fingers 142. As before, the spring fingers 142 include exterior plunger retaining surfaces 144 and interior plunger releasing surfaces 146. As shown, the rearward end wall 30 of the outer housing member 28 is apertured to receive the second plunger 136 and includes cooperating rearwardly and inwardly facing plunger retaining surfaces 148. In this regard, it will be noted that the end wall 30 is also apertured, as indicated at 150, to allow free movement of the first plunger 116 therethrough. Similarly, the end wall 44 of the inner housing member 42 is apertured, indicated at 152, to receive a forwardly extending skirt 154 which surrounds the rearward end portion of a stresed coil spring 156, the forward end of which engages the flange 138 and the rearward end of which engages the forward surface of the end wall 30 of the outer housing member 28 surrounded by the skirt 154.

Mounted within the interior plunger releasing surfaces 146 of the fingers 142 of the second plunger 136 is a second releasing pin, generally indicated at 158. The releasing pin 158 is of the type adapted to release the spring fingers 142 either when moved forwardly or rearwardly with respect to the rear end of the associated spring fingers. As shown, the releasing pin 158 includes a forward movement preventing portion 160 which has a diameter sufficient to engage with the interior plunger releasing surfaces 146 so as to be disposed in engagement therewith when the plunger 136 is in its storage position. The releasing pin 158 also includes an actuating button 162 spaced rearwardly from the movement perventing portion 160 and movable forwardly to move the latter out of its storage position into a releasing position or movable rearwardly to remove the movement preventing portion 160 from its storage position. To enable the forward releasing function to take place, the releasing pin 158 includes a movement preventing portion 164 of reduced diameter fixed between the movement preventing portion 160 and the actuating button 162.

In addition to the releasing pins 130 and 158, the assembly 26 also includes a safety cap 166 which is formed as an end wall having an annular skirt extending forwardly thereof. The forward end of the skirt is recessed so as to engage over the rearward end portion of the outer housing member 28 and to provide an annular shoulder 168 which engages the marginal peripheral portion of the rear wall 30. As shown, the releasing pin 130 is detachably fixed with the end wall of the safety cap 166, as by a screw 170.

The apparatus 10 is assembled by first assembling the first stressed spring assembly 22 in operative relation with the end wall 44 of the inner housing member 42. This is accomplished by moving the plunger 116 rearwardly within the inner housing member 42 until the rearward end of the plunger fingers 122 engaged through the opening defined by the plunger retaining surfaces 126. The releasing pin 130 is then inserted within the fingers 122 to prevent them from moving radially inwardly. In this way the plunger 116 is prevented from moving forwardly by virtue of the intergagement between the plunger retaining surfaces 124 and 126 thus retaining the coil spring 132 in its stressed condition. Similarly, the second stressed spring assembly 24 is mounted in operative relation with respect to the outer housing member 28 utilizing releasable pin 158. Next, the safety cap 166 is engaged into its storage position and screw 170 is threaded into secured relation within the releasing pin 130 so that the latter will be moved out of its storage position in response to the rearward movement of the safety cap 166 out of its storage position, as shown in FIG. 1.

Next, the containers 76 and 78 are separately filled with the respective medicament ingredients 104 and 108 and sealed with the diaphragms 90 and 100 by the hub assemblies 92 and 102 at their forward ends and with the pistons 106 and 110–112 at their rearward ends. Next, the two containers are mounted within the container support structure 80 and then the hub assemblies 92 and 102 are moved into an initial position with respect to the cylindrical portions 62 and 68 of the member 48. After the resilient sheath 52 has been mounted over the needle element 50 the entire unit containing the two container assemblies 18 and 20, the inner housing structure 14 and needle assembly 16 is moved rearwardly into the outer tubular housing member 28 and the forward housing member 36 is snapped over the forward end thereof to complete the assembly.

To operate the apparatus 10 the operator first moves the safety cap 166 out of its storage position, as shown in FIG. 1. This movement preferably is accomplished by simply pulling the cap 166 off of its engagement with the outer housing member 28. The removing of the safety cap 166 carries with it the safety pin 130 and this movement constitutes the first predetermined actuating movement which effects the release of the first stressed spring assembly 22. In this regard, it will be noted that the angle of the plunger movement preventing surfaces 124 and 126 are such that as soon as the releasing pin 130 is removed from its storage position, the stress of the spring 132 will effect sufficient forward movement of the plunger 116 to cause the spring fingers 122 to be moved radially inwardly until the surfaces 124 disengage from the surfaces 126 and then the stressed spring 132 is capable of advancing the plunger 116 forwardly through an operative stroke. Since the flange 118 or the forward end of the plunger 116 is in engagement with the piston 106 which in turn is in engagement with the liquid medicament ingredient 104 within the container 76, the initial forward movement of the plunger 116 will result in a forward movement of the entire container 76 and the container support structure 80 by virtue of the engagement of the forward shoulder 86 thereof with the container 76. Similarly, this forward movement of the container support structure 80 has the effect of moving the second container 78 forwardly by virtue of the rearward flange 96.

Thus, the initial movement of the plunger 116 results in a forward movement of both containers 76 and 78 and the container support structure 80. During this forward movement, the hub assemblies 92 and 102 telescope with respect to the cyclindrical portions 62 and 68 allowing the associated diaphragms 90 and 100 to move fowardly in piercing relation to the associated piercing elements 64 and 70. Forward movement of the two containers and container support structure together is positively limited by the engagement of the forward end of the hub portions 92 and 102 with the rear surface of the inner housing member 48 which in turn is held against forward movement by the engagement of the needle assembly 16 with the outer housing assembly 12. When the diaphragms 90 and 100 are pierced, the interior of the two containers 76 and 78 are communicated with each other through passage 60, cross passage 56 and passage 66. Consequently, further forward movement of the plunger 116 under the action of the released stressed spring 132 results in the forward movement of the piston 106 within container 76 which has the effect of expelling the liquid medicament ingredient 104 from the container 76 into the second container 78 so as to mix with the medicament ingredients 104 and 108 contained therein to form liquid medicament and effect a rearward movement of the piston 110.

It will be noted that because the second stressed spring assembly 24 is retained in operative postion with respect to the outer housing assembly 12, the flanged end 138 of the second plunger 136 assumes a position rearwardly of the second container 78 by virtue of the aforesaid forward movement of the second container 78 with the container support structure 80 during the initial movement of the first plunger 116. Consequently, as the forward piston 110 moves rearwardly, the air trapped between the forward piston 110 and the vent piston 112 tends to increase in pressure thus causing the vent piston 112 to be moved rearwardly into a position of engagement with the flanged end 138 of the second plunger 136. When the vent piston 112 is in such an engagement, the vent slots 114 vent the interior space of the container 78 rearwardly of the piston 110 to atmosphere thus enabling the same to move rearwardly as the liquid medicament ingredient from the first container flows into the second container. As best shown in FIG. 2, at the end of the operative stroke of the first plunger 116, substantially the entire amount of liquid medicament ingredient 104 within the first container 76 has been transferred into the second container 78 and mixed with the powder medicament ingredient 108 therein to form liquid medicament.

It may be recommended that the operator at that point actually shake the apparatus 10 to insure that all the mixing of the medicament ingredients has taken place to form liquid medicament to be injected. Injection is accomplished in response to a second predetermined actuating procedure which includes the operator gripping the exterior periphery of the outer housing member 28 and moving the nose portion 40 into engagement with the patient's skin in the area which is to receive the injection, as for example, the thigh. Next, the operator simply pushes forwardly on the actuating button 162, as with the thumb, which has the effect of releasing the second stressed spring assembly 24. As before, the movement of the releasing pin 158 out of its storage position permits the stressed spring 156 biasing the plunger 136 forwardly to effect a radially inward movement of the plunger fingers 142 by virtue of the interengagement between the plunger retaining surfaces 144 and 148. As the plunger 136 moves forwardly under the action of the released stressed spring 156 the forward flanged end 138 of the plunger 136 in engagement with the vent piston 112 tends to move the latter forwardly which in turn is in engagement with the piston 110 acting on the rear end of the liquid medicament within the container 78. The initial movement of the plunger therefore applies a force to the liquid medicament which tends to cause the same to move outwardly of the second container and into the passage 66. While the liquid medicament may move through the cross passage 56 and rearwardly into the passage 60 into the first container 76, this flow path is greatly restricted due to the residual spring force acting on the first piston 106 by the released first spring 132. The resistance to flow outwardly of the passage 54 through the needle element 50 is prevented by virtue of the blockage of the forward end of the passage 54 by the resilient sheath 52. The resistance to the movement of the sharpened forward end of the needle element 50 and the entire inner housing assembly 14 including the two container assemblies 18 and 20 carried thereby is less than the hydraulic resistance and consequently, the applicaton of the force of spring 156 through the plunger 136, pistons 112 and 110 to the liquid medicament in the second container 78 is transmitted to the inner housing assembly 14 through the engagement of the hub assemblies 92 and 102 with the member 48, results in the movement of the needle element 50 forwardly through the resilient sheath 52 and outwardly of the outer housing portion 40 into the muscle tissue of the patient.

The forward movement of the inner housing assembly 14 with respect to the outer housing assembly 12 is arrested by virtue of the compression of the resilient sheath 52. When the forward movement of the inner housing structure 14 is arrested by the compression of the sheath, continued forward movement of the plunger 136 under the bias of the spring 156 serves to advance the two pistons 112 and 110 within the container 78 thus expelling the liquid medicament therein outwardly through the passage 66, the cross passage 56 and the passage 54 in the needle element 50 into the muscle tissue of the patient. In this way, substantially the entire amount of the liquid medicament within the second container 78 is injected into the muscle tissue of the patient, as shown in FIG. 3. As soon as the injection has been completed the operator simply withdraws the needle element 50 from the patient.

Referring now more particularly to FIGS. 5 and 6 of the drawings, there is shown therein another form of apparatus, generally indicated at 210 which embodies the principals of the present invention. The apparatus 210 is similar to the apparatus I0 except that the containers are fixed with respect to the inner housing structure and the safety cap and the releasing assembly is of a different form.

As shown, the apparatus 210 includes an outer housing assembly 212, an inner housing structure 214 mounted within the outer housing assembly for movement forwardly from a storage position into an injecting position. A hypodermic needle assembly 216 is fixed to the forward central portion of the inner housing structure 214 within the outer housing assembly 212 in a sterile condition disposed in a storage position when the inner housing structure 214 is in its storage positon and capable of moving outwardly of the outer housing assembly 212 with the inner housing structure 214 for movement into the muscle tissue of a patient when the inner housing structure moves into its injecting position.

Embodied within the inner housing structure 214 is a first medicament container assembly 218 and a side-by-side second medicament container assembly, generally indicated at 220. Operatively associated with the first medicament container assembly 218 and with the inner housing structure 214 is a first stressed spring assembly, generally indicated at 222. A second stressed spring assembly 224 is operatively connected with the second medicament container assembly 220 and with the outer housing assembly 212. As before, a safety cap and releasing assembly, generally indicated at 226, is provided in a storage position for rendering the first and second stressed spring assemblies 222 and 224 incapable of being released. When moved out of its storage position the assembly 226 enables the first stressed spring assembly 222 to be released in response to a first predetermined actuating procedure and then the second stressed spring assembly 224 to be released in response to a second predetermined actuating procedure.

The outer housing assembly 212 is similar to the outer housing assembly 12 previously described in that it includes a main tubular outer housing member 228 having a rear end wall 230 at its rearward end and being open at its forward end. The forward end is closed by a forward housing member 232 which includes a rearwardly extending annular skirt having an interior annular ridge formed therein for engaging within a cooperating annular groove formed in the periphery of the forward end portion of the outer housing member 228. The forward outer housing member 232 also includes a forwardly projecting skin engaging nose portion 234 which is centrally apertured to permit movement of a needle 236 therethrough forming a part of the needle assembly 216.

The inner housing structure 214 includes an inner tubular housing member 238 having an exterior peripheral configuration to slidably engage within the interior peripheral configuration of the outer housing member 228. The inner housing member includes an end wall 240 at its rearward end and, like the outer housing member 228 is open at its forward end. The inner housing structure 214 includes an inner housing member 242 which provides a forward wall having an exterior annular ridge for engaging within an interior peripheral groove formed on the forward end portion of the inner housing member 242. The inner housing member 242 also includes a rearwardly extending portion defining a first container 244 extending rearwardly within the housing member 234 and a second container 246 in side-by-side relation with respect to the first container 244.

It will be noted that the hypodermic needle is of conventional metal configuration having a sharpened forward edge which is engaged within the tip of a resilient sheath 248 so as to close off communication of the hollow interior thereof. The rearward end of the needle communicates with a rearwardly extending passage 250 which is formed in the central forward portion of the inner housing member 242. The rearward end of the passage 250 communicates with the intermediate portion of a cross passage 252, one end of which communicates with the forward end of a passage 254 extending rearwardly in communication with the interior of the first container 244. The first container 244 includes therein a liquid medicament ingredient 256 which is sealingly confined rearwardly by a piston 258 of suitable resilient material so as to be slidably sealingly mounted within the container 244.

The opposite end of the cross passage 252 communicates with a counterbore 260 formed in the forward portion of the member 242. The end of the counterbore 260 is closed by a detachable plug 262. Mounted within the counterbore 260 is a piston valve 264 which, as shown in FIG. 5, is disposed in a storage position closing off communication between the associated end of the cross passage 252 and a short passage 266 extending from the counterbore rearwardly into communication with the second container 246. Mounted within the forward end portion of the second container 246 is a medicament ingredient 268 which preferably is in dry form, specifically a freeze dried powder. The medicament ingredient 268 is sealingly retained within the second container by a piston 270 which is of suitable resilient material like the piston 258 previously described. Mounted in the rearward end portion of the second container 246 in rearwardly spaced relation to the forward piston 270 is a vent piston 272. The vent piston 272 is normally disposed in a storage position spaced inwardly from the rearward end of the second container 246. Formed in the interior periphery of the rearward end portion of the second container 246 is a plurality of annularly spaced vent grooves 274 which extend from the rearward end portion of the piston 272 to the rearward end of the second container 246.

The first stressed spring assembly 222 includes a hollow plunger 276 the forward end of which is flanged, as indicated at 278, and disposed in engagement with the first piston 258 forming a part of the first container 218. The rearward portion of the plunger 276 is slotted, as indicated at 280, to form a plurality of annularly spaced resilient fingers 282 which are integral with the plunger. The fingers 282 are formed with exterior plunger retaining surfaces 284 which face forwardly and outwardly and extend at an angle of approximately 45°. It will be noted that the rearward end wall 240 of the inner housing member 238 is apertured to receive the plunger 276 and is provided with cooperating interior plunger retaining surfaces 286 which face inwardly and rearwardly and extend at an angle of approximately 45°. The fingers 282 of the plunger 276 are also provided with a series of interior plunger releasing surfaces 288. These surfaces are disposed within a common cylindrical plane which has a diameter substantially less than the interior diameter of the hollow piston. The interior plunger releasing surfaces 288 extend from the rearward end of the fingers inwardly a short distance. Mounted within the interior plunger releasing surfaces 288 of the fingers 282 is a first releasing pin 290 which, as shown, forms a part of the safety cap and releasing assembly 226.

It will be understood that when the releasing pin 290 is disposed in engagement with the interior plunger releasing surfaces 288 the associated fingers 282 are prevented from being deflected radially inwardly. The releasing pin 290 thus serves to insure that the exterior plunger retaining surfaces 284 of the fingers 282 will be maintained in engagement with the cooperating plunger retaining surfaces of the inner housing structure 214. This maintainance is provided notwithstanding the bias which is present by virtue of a stressed coil spring 292 forming a part of the spring assembly 222. Coil spring 292 is mounted over the exterior periphery of the plunger 276 with its forward end in engagement with the flange 278 and its rearward end in engagement with the forwardly facing surface of the rearward end wall 240 of the inner housing structure 214. In order to center the coil spring 292, preferably the end wall 240 is provided with an integral forwardly extending cylindrical skirt portion 294 which surrounds the rearward end portion of the coil spring 292.

The second stressed spring assembly 224 is similar to the first in that it includes a hollow plunger 296 having a flange 298 on the forward exterior periphery thereof and slots 300 formed in the rearward end portion thereof so as to define a series of annularly spaced radially inwardly deflectable spring fingers 302. As before, the spring fingers 302 include exterior plunger retaining surfaces 304 and interior plunger releasing surfaces 306. As shown, the rearward end wall 320 of the outer housing member 228 is apertured to receive the second plunger 296 and includes cooperating rearwardly and inwardly facing plunger retaining surfaces 308. In this regard, it will be noted that the end wall 230 is also apertured to allow free movement of the first plunger 276 therethrough. Similarly, the end wall 240 of the inner housing member 238 is apertured to receive a forwardly extending skirt 309 which surrounds the rearward end portion of a stressed coil spring 310, the forward end of which engages the flange 298 and the rearward end of which engages the forward surface of the end wall 230 of the outer housing member 228 surrounded by the skirt 309.

Mounted within the interior plunger releasing surfaces 306 of the fingers 302 of the second plunger 296 is a second releasing pin, generally indicated at 312. The releasing pin 312 is of the type adapted to release the spring fingers 302 either when moved forwardly or rearwardly with respect to the rear end of the associated spring fingers. As shown, the releasing pin 312 includes a forward movement preventing portion 314 which has a diameter sufficient to engage with the interior plunger releasing surfaces 306 so as to be disposed in engagement therewith when the plunger 296 is in its storage position. The releasing pin 312 also includes an actuating button 316 spaced rearwardly from the movement portion 314 and movable forwardly to move the latter out of its storage position into a releasing position or movable rearwardly to remove the movement preventing portion 314 from its storage position. To enable the forward releasing function to take place, the releasing pin 312 includes a movement enabling portion 318 of reduced diameter fixed between the movement preventing portion 314 and the actuating button 316.

In addition to the releasing pins 290 and 312, the assembly 226 also includes a safety key 320 and a safety cap 322 which is formed as an end wall having a manually engagable annular skirt 324 extending forwardly thereof over a substantial portion of the outer housing member 228. The key 320 is in the form of a rearward wall which is integrally connected with the rear end of the pin 290. The key 320 also includes a cylindrical wall portion 326 extending forwardly from the rear wall and a keyed or dual lug shaped wall portion 328 extending forwardly from the portion 326. Formed in the rear wall of the safety cap 322 is a keyed or dual lug shaped opening 330 of a size to receive the keyed portion 328 therethrough which is rotationally aligned therewith. It will be noted however that when the safety key 320 is turned into the storage position shown so as to be rotationally out of alignment, the keyed portion 328 extends between the cap end wall and the outer housing member end wall so as to prevent forward movement of the cap 322 out of its storage position as shown.

The apparatus 210 is assembled by first assembling the first stressed spring assembly 222 in operative relation with the end wall 240 of the inner housing member 238. This is accomplished by moving the plunger 276 rearwardly within the inner housing member 238 until the rearward end of the plunger fingers 282 engage through the opening defined by the plunger retaining surfaces 286. The releasing pin 290 carried by the safety key 320 is then inserted within the fingers 282 to prevent them from moving radially inwardly. In this way the plunger 276 is prevented from moving forwardly by virtue of the interengagement between the plunger retaining surfaces 284 and 286 thus retaining the coil spring 292 in its stressed condition. Similarly, the second stressed spring assembly 224 is mounted in operative relation with respect to the outer housing member 228 utilizing releasable pin 312. Next, the safety cap 322 is engaged into its storage position with skirt 324 extending over the outer housing member 228 and with the opening 330 receiving the portion 326 of the key 320. Forward movement of the cap is stopped by the engagement of the keyed portion 328 of the safety key 320 between the cap rear wall and the housing member rear wall.

Next, the containers 244 and 246 are separately filled with the respective medicament ingredients 256 and 268 and sealed by the piston valve 266 and plug 262 at their forward ends and with the pistons 258 and 270-272 at their rearward ends. Next, the housing member 242 defining the two containers is mounted within the inner housing member 238 and needle 236 is mounted in place. After the resilient sheath 248 has been mounted over the needle 236, the entire unit containing the two container assemblies 218 and 220, the inner housing structure 214 and needle assembly 216 is moved rearwardly into the outer tubular housing member 228 and the housing member 232 is snapped over the forward end thereof to complete the assembly.

To operate the apparatus 210 the operator first turns the safety key 320 and moves it rearwardly out of its storage position, as shown in FIG. 5. The removal of the safety key 320 carries with it the safety pin 290 and this movement constitutes the first predetermined actuating procedure which effects the release of the first stressed spring assembly 222. In this regard, it will be noted that the angle of the plunger movement preventing surfaces 284 and 286 are such that as soon as the releasing pin 290 is removed from its storage position, the stress of spring 292 will effect sufficient forward movement of the plunger 276 to cause the spring fingers 282 to be moved radially inwardly until the surface 284 disengages from the surface 286 and then the stressed spring 292 is capable of advancing the plunger 276 forwardly through an operative stroke.

Since the forward flanged end 278 of the plunger 276 is in engagement with piston 258 which in turn is in engagement with the liquid medicament ingredient 256, the force of the released stressed spring 292 serves to increase the pressure within the liquid medicament ingredient 256. This pressure is transmitted to the inner housing member 242 and the liquid within the passage 254 and cross passage 252 therein. The force required to effect movement of the piston valve 264 is considerably less than the force required to effect movement of the entire inner housing member 214 and consequently the piston valve 264 w111 be moved into a position uncovering the passage 266 so as to allow the pressurized liquid medicament ingredient 256 to pass into the second container 246 to mix with the medicament ingredient 268 therein. As the liquid medicament ingredient 256 flows into the second container 246 piston 270 will be moved rearwardly. This movement in turn causes the air rearwardly of the piston to increase and this increase in pressure in turn builds up until it is sufficient to effect a rearward movement of the vent piston 272. The vent piston 272 moves rearwardly until it engages the forward flanged end 298 of the plunger 296. In this position vent grooves 274 are communicated with the space within the second container 246 forwardly of the vent piston 272 thus exhausting the pressure to atmosphere and allowing the piston 270 to move freely rearwardly in response to the flow of liquid medicament ingredient 256 from the first container into the second container. When this movement has been completed by virtue of the movement of the piston 258 into its forwardmost postion, the operator may at that time shake the apparatus to insure that the liquid medicament 256 will be mixed thoroughly with the medicament ingredient 268 within the second container.

Next, the operator performs the second predetermined manual actuating procedure which has the effect of injecting the liquid medicament formed during the mixing operation. The actuating procedure includes grasping the skirt 324 of the safety cap 322 and moving the nose portion 234 of the outer housing assembly 212 into engagement with the skin of the patient in the area which is to receive the injection, as for example, the thigh. Continued forward movement on the skirt 324 has the effect of effecting the forward movement of the latter with respect to the outer housing assembly 212 during which movement the rear wall of the safety cap 226 will engage the actuating button 312 and move the same forwardly until movement preventing portion 314 thereof is disengaged from the movement preventing surfaces 306 of the spring fingers. Immediately thereafter the force of spring 310 and the inclination of the surfaces 304 and 308 are such as to cause the plunger 296 to move forwardly deforming the spring fingers 302 radially inwardly until surfaces 304 are disengaged from the surfaces 308. Continued forward movement of the plunger 298 acts through vent piston 272, piston 270 and the liquid medicament forwardly thereof to move the inner housing structure 214 forwardly. During the initial forward movement of the inner housing structure 214, needle 236 pierces through the end of the resilient sheath 248 and extends outwardly beyond the housing nose portion 234 into the muscle tissue of the patient. This outward movement is arrested by the compression of the resilient sheath 248 against the housing portion 234. As soon as the forward movement of the inner housing structure 214 is arrested, continued forward movement of the plunger 296 will result in an outward movement of the liquid medicament forward of the plunger 270 outwardly of the second container through passage 266, cross passage 252, passage 250 and into the hypodermic needle 236 and finally outwardly into the muscle tissue of the patient. This movement of the liquid ingredient from the container 246 into the muscle tissue of the patient continues until the piston 270 reaches its forwardmost position within the container. As soon as this injection procedure has been accomplished, the operator simply removes the device from the patient and in this fashion withdraws the needle from the muscle tissue.

Figure 8:
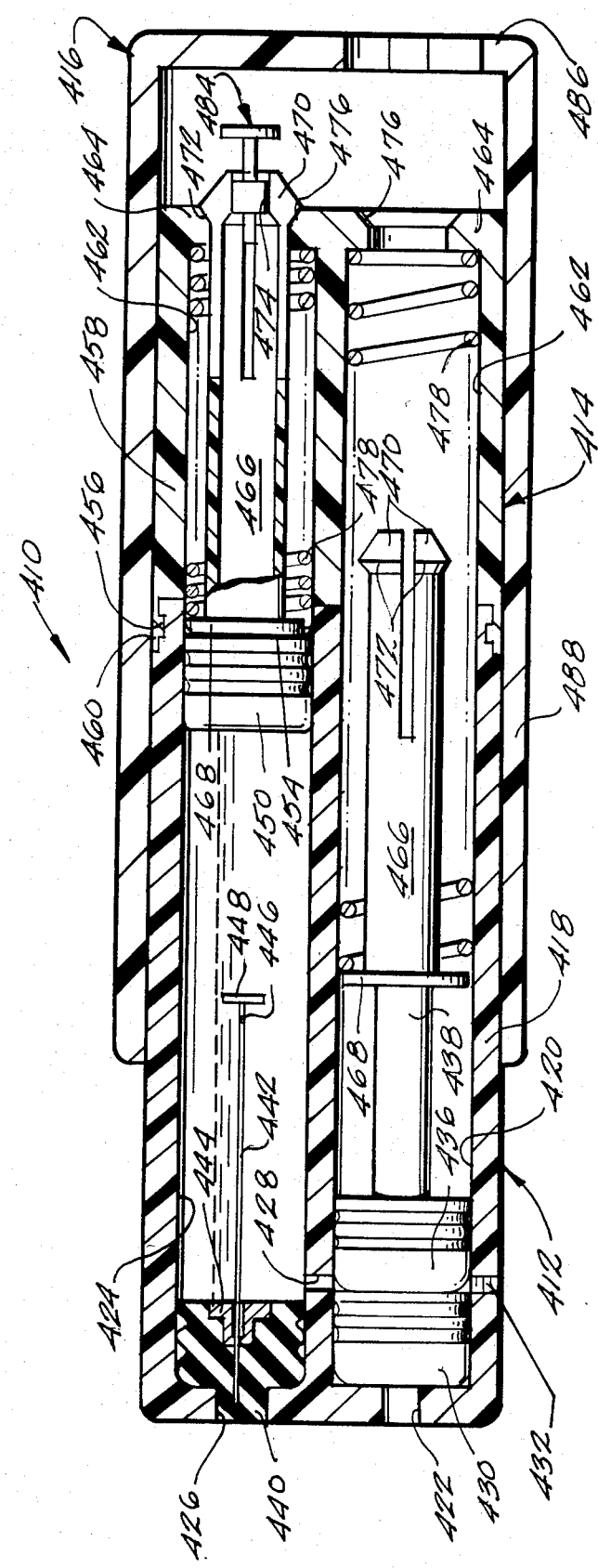
FIG. 8 is a view similar to FIG. 2 of the apparatus shown in FIG. 7.
Figure 9:
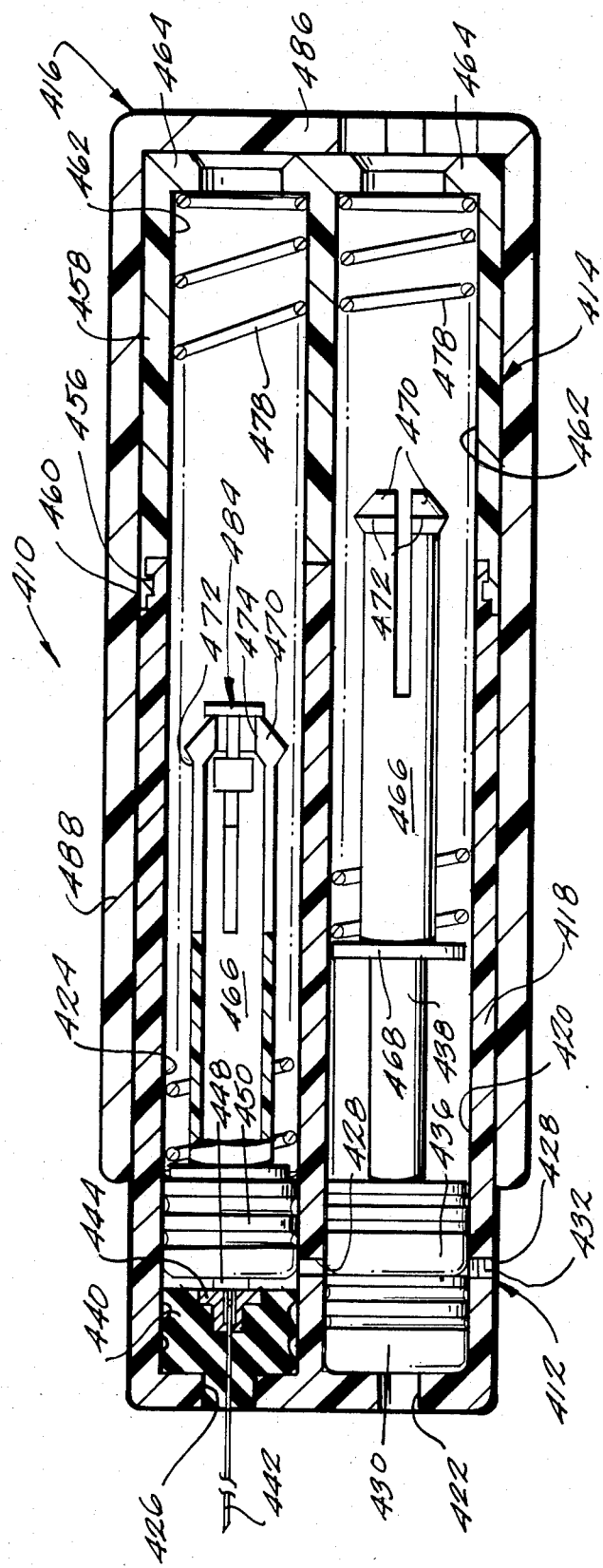
FIG. 9 is a view similar to FIG. 3 of the apparatus shown in FIG. 7.

Referring now more particularly to FIGS. 7 through 9, there is shown therein still another form of automatic injecting apparatus, generally indicated at 410 which embodies the principles of the present invention. The apparatus 410 differs from the apparatus 10 and the apparatus 210 previously described in that the injecting function is accomplished in accordance with the structural and functional principles enunciated in commonly assigned U.S. Pat. No. 3,396,726, the disclosure of which is hereby incorporated by reference into the present specification. As shown, the apparatus 410 consists essentially of a plural cartridge assembly, generally indicated at 412, a plural releasable stressed spring assembly, generally indicated at 414, and a safety cap and releasing pin assembly, generally indicated at 416.

The plural cartridge assembly 412 includes a housing member 418 which is in the form of a molded plastic body providing a first cylindrical cavity 420 which is open at its rearward end and closed at its forward end except for a central vent opening 422. The housing member 418 also provides a second cylindrical cavity 424 which is open at its rearward end and closed at its forward end except for a central opening 426. Formed in the portion of the housing member 418 defining the forward end portion of the first cavity 420 is a bore 428 which extends transversely through the periphery of the housing body radially inwardly into the cavity 420 and radially outwardly thereof into the second cavity 424 at a position spaced from the forward end thereof.

Mounted within the first cavity 420 is a piston valve 430 which in its storage position, shown in FIG. 7, extends forwardly and rearwardly of the bore 428 so that its forward surface is spaced from the forward end of the cavity 420. A plug 432 is formed in the outer portion of the bore 428 so as to close off the same and prevent flow of liquid outward of the first cavity therethrough. The piston valve 430 which is molded of a suitable resilient material, as for example, an elastomeric resin or rubber, defines the end of a medicament container within the housing member 418 within which a liquid medicament ingredient 434 is contained. The rearward end of the liquid medicament ingredient 434 is confined by a piston 436 which, like the piston valve 430, is formed of a suitable resilient material. Detachably secured by the piston 436 and extending rearwardly therefrom is a spacer 438 having its rearward end disposed adjacent the rearward open end of the first cavity 420.

Mounted in the forward end of the second cavity 424 in filling relation to the opening 426 is a piston or plug member 440 of resilient material within which is received the sharpened end of a hypodermic needle 442, as by an inset fitting 444. The hypodermic needle 442 is hollow and includes a lateral opening 446 in its rearward end portion and a flattened disk-like element 448 on its rearward end which is disposed in engagement with a piston 450 similar to the piston 436. The second cavity 424, between the forward piston plug 440 and rearward piston 450, defines a second medicament container within which is mounted a medicament ingredient 452 preferably in the form of a dry powder although it may be in liquid form if desired. Mounted in the open rear end of the second cavity 424 is a disk shaped flap valve element 454 which acts as a sterility check valve for the portion of the cavity 424 between the valve element 454 and the piston 450.

The rearward exterior periphery of the housing member 418 is recessed and formed with an annular groove 456. The plural stressed spring assembly 414 includes a housing member 458 which, like the housing member 418, is in the form of a molded plastic body which includes an interiorly ridged peripheral skirt 460 extending from the forward end thereof for engagement within the groove 456 as by a snap fit. The two housing members 418 and 458 once assembled constitute an outer housing assembly of the apparatus 410.

The housing member 458 of the spring assembly 414 is formed with two cylindrical cavities 462 which are open at their forward ends and partially closed at their rearward ends as by centrally apertured rear wall portions 464. The assembly 414 further includes components which make up two stressed spring assemblies similar to the stressed spring assemblies 22 and 24 and 222 and 224 previously described. Thus each of the two stressed spring assemblies includes a plunger 466 having a flanged forward end 468 and a split rearward end portion defining radially inwardly deformable fingers 470 having exterior plunger retaining surfaces 472 and interior plunger releasing surfaces 474. The apertured rear wall portions 464 are formed with corresponding plunger retaining surfaces 476 and a stressed coil spring 478 surrounds each plunger 466 with its ends engaging the associated flanged forward end 468 thereof and the associated rear wall portion 464.

Similarly, the safety cap and releasing pin assembly 416 is similar to the assembly 226 previously described. As before, a safety key 480 having an integral releasing pin 482 engageable with the releasing surfaces 474 of the first plunger 466 is provided and a second releasing pin 484 similar to the releasing pin 312 previously described is mounted in operative relation with respect to the releasing surfaces 474 of the second plunger 466. Extending over the outer end portion of the rearward housing member 458 is a safety cap 486 which has a keyed opening for receiving the safety key 480 and an elongated skirt 488 capable of being gripped by the operator.

The assembly of the automatic injecting apparatus 410 will be readily apparent in that the cartridge assembly 412 is assembled with the components thereof being inserted forwardly into the cavities 420 and 424 from the rear end thereof while the spring assemblies are assembled in the housing member 458 by moving the components rearwardly into the forward end of the cavaties 462. Once the releasing pins 482 and 484 are in place, the two housing members 418 and 458 are snapped together and then the safety cap 486 is moved over the rear of the entire assembly.

The apparatus 410 is operated in a manner similar to the apparatus 210 in that the first manual actuating procedure is to turn and remove the safety key 480 which releases the first stressed spring 478. The release of the first spring accomplishes the mixing of the liquid medicament ingredient 434 with the powder medicament ingredient 452. The second manual actuating procedure is for the operator to grasp the elongated safety cap skirt 488 and move the forward end of the outer housing assembly into engagement with the skin of the patient at the location where the injection is to take place. As a result of this actuating procedure the hypodermic needle 442 is extended into the muscle tissue of the patient and the liquid medicament which has previously been formed is injected through the needle 442 into the muscle tissue of the patient.

It will be noted that when the first stressed spring 478 is released from the storage position shown in FIG. 7 by the withdrawal of the safety key 480 the force of the spring will be applied through spacer 438 to the piston 436 which, in turn, is applied to the liquid medicament ingredient 434 which, in turn, acts upon the piston valve 430. The piston valve 430 therefore moves forwardly until it engages the forward wall within which the vent aperture 422 is formed. When the piston valve 430 reaches this position the inner portion of the communicating bore 428 serves to communicate the liquid medicament ingredient 434 with the cavity 424 within which the powder medicament ingredient 452 is mounted. As the liquid flows into this container, the air space within the container is compressed thus tending to move the piston 450 rearwardly. As the piston 450 moves rearwardly the air within the space within the cavity 424 between the piston 450 and the flap valve element 454 will increase slightly to a value which is sufficient to cause the flap valve element 454 to move rearwardly and communicate the space rearwardly of the piston 450 with the atmosphere. In this way, the piston 450 is capable of being moved rearwardly into a position of engagement with the forward end of the valve element 454 and the plunger end 468 without generating any air pressure acting in a direction to move the piston 450 forwardly.

When the piston reaches its rearwardmost position, shown in FIG. 8, substantially all of the liquid medicament ingredient 434 has been moved into the second container for mixing with the dry medicament ingredient 452 therein. However, due to the initial presence of the air within the second container, an equivalent amount of air remains between the forward piston plug 440 and the rear piston 450, as shown in FIG. 8. The existence of this air within the cavity is essential to the proper functioning of the apparatus 410 during the drive stroke of the second plunger 466 when the second stressed spring 478 is released.

During the initial portion of the forward movement of the piston 450 with the plunger 466 from the position shown in FIG. 8 the air within the second container will be compressed forwardly of the piston 450. Such air compression will continue to occur as the piston 450 moves forwardly until such time as the pressure reaches a value sufficient to cause flow of liquid out of the container through the bore 428 into the first cavity 420 moving the piston 436 back against the residual spring pressure of the first spring 478. The arrangement is such that it is preferable that when the piston 450 reaches the rear end of the hypodermic needle there will be a pocket of air forwardly of the piston whose axial dimension is equal to the distance the sharpened end of the needle 442 must travel to enter within the muscle tissue of the patient. As previously indicated, the containment of such a volume of air may require the outflow of liquid medicament from the second container through the bore 428 into the first container.

When the piston 450 reaches the end of the hypodermic needle in the position shown in FIG. 8, further forward movement of the piston 450 will result in a forward movement of the hypodermic needle 442 with the piston. In this way the needle 442 is moved into the muscle tissue of the patient and it will be noted that as the needle begins to move into the muscle tissue of the patient the liquid medicament forwardly of the piston also begins to flow into the needle opening 446 for passage therethrough outwardly into the muscle tissue of the patient. When the piston 450 reaches the forward end of its travel, as shown in FIG. 9, it is still possible for any liquid which may have moved into the first cavity 420 in a position forwardly of the piston 436 to be moved outwardly of the first cavity 420 through the bore 428 and finally into the needle 442 and out into the muscle of the patient. As before, when the injection has been completed the operator simply removes the apparatus rearwardly which has the effect of removing the needle 442 from the patient.

Referring now more particularly to FIGS. 10 through 13 there is shown therein still another form of an automatic injecting apparatus, generally indicated at 510, which embodies the principles of the present invention. The apparatus 510 exemplifies that the principles of the present invention can be carried out with only one stressed spring assembly and with the medicament ingredient containers disposed in arrangements other than side by side. Specifically, in the apparatus 510 the containers are telescopically mounted and it will be understood that other arrangements can be utilized in practicing the principles of the present invention.

The apparatus 510 includes an outer housing assembly, generally indicated at 512 within which is mounted a dual container cartridge assembly 514 and a single stressed spring assembly 516. The apparatus 510 also includes a safety cap and releasing pin assembly 518 which is operable in response to a first predetermined manual actuating procedure to effect a first release of the stressed spring assembly 516 for effecting the mixing function and a second releasing assembly 520 operable in response to a second predetermined manual actuating procedure to effect a second release of the stressed spring assembly 516 for effecting the injecting function.

As shown, the outer housing assembly 512 includes a tubular housing member 522 in the form of a cylinder having an open forward end and a rearward end closed by an end wall 524 having a central opening therein. The housing assembly 512 also includes a forward housing member 526 which includes a rearwardly extending skirt 528 having a snap connection over the exterior periphery of the forward end of tubular frame member 522 and a central forwardly extending nose portion 530 which is centrally apertured.

The dual container cartridge assembly 514 includes an outer container 532 which is in the form of a cylindrical container open at its rearward end and having a necked down exteriorly flanged forward end. A hub assembly 534 serves to connect the rear end of a hypodermic needle 536 in communicating relation with the forward necked down end of the container 532. A resilient sheath 538 is fixed over the hypodermic needle 536 and its tip serves to sealingly retain liquid within the hypodermic needle 536 while in its storage condition and to retain the hypodermic needle in a sterile condition.

Mounted in the forward end of the outer container 532 is a medicament ingredient 540 preferably in the form of dry powder. The medicament ingredient 540 is confined at its rearward end by a large piston 542 which has a deep recess 544 formed in the rear end portion thereof so as to define a thin forward central portion in the piston 542. Mounted within the outer container 532 rearwardly of the piston 542 is an inner container 546 which is of a configuration similar to the configuration of the container 532 but of smaller diameter. The necked down exteriorly flanged forward end portion of the inner container 546 is connected, as by a hub assembly 548 to a short needlelike element 550, the sharpened end of which is embedded within the central thin wall portion of the piston 542 so as to provide a liquid seal thereof.

Figure 10:
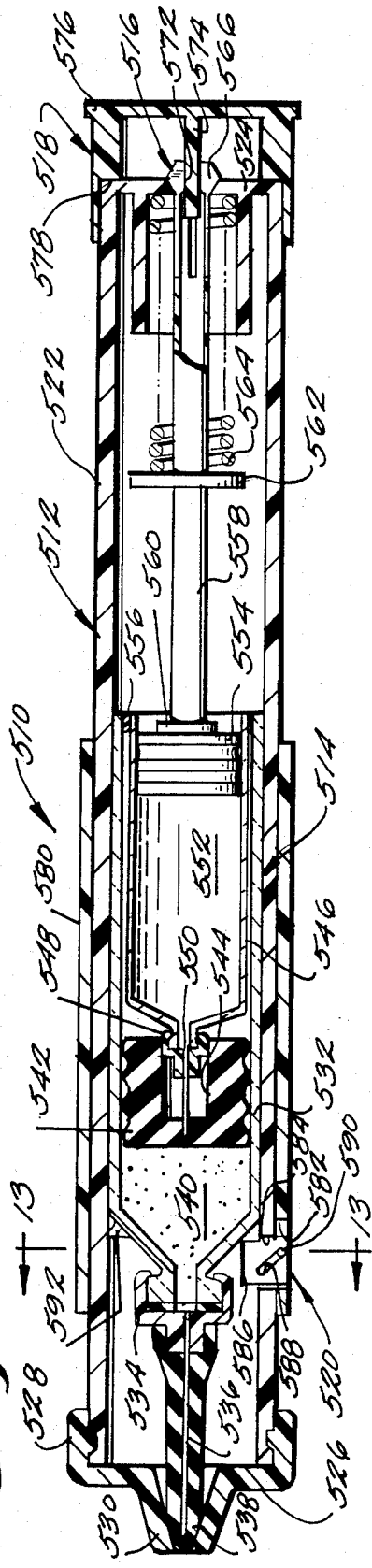
FIG. 10 is a view similar to FIG. 1 of still another form of automatic mixing and injecting apparatus embodying the principles of the present invention.

Mounted within the inner container 546 is a liquid medicament ingredient 552 which is confined at its rear end by a piston 554 of resilient material. As best shown in FIG. 10, there is a blowout ring seal 556 provided in the rear end of the two containers 532 and 546 for maintaining the interior of the outer container 532 between the rear seal 556 and the piston 542 in a sterile condition when the apparatus 510 is in its storage position, as shown in FIG. 10.

The stressed spring assembly 516 includes an elongated plunger 558 having a flanged forward end 560 arranged to be disposed in engagement with the piston 554 and an intermediate flange 562 for receiving one end of a stressed coil spring 564, the opposite end of which engages the rear end wall 524 of the outer tubular housing member 522. The rear end portion of the plunger 558 is slotted to form a plurality of spring fingers 566 which have plunger retaining surfaces 568 arranged to be engaged with a frustoconical plunger retaining surface 570 in the end wall 524 and interior plunger releasing surfaces 572 which, as shown in FIG. 10, engage the exterior of a releasing pin 574 forming a part of the assembly 518. As best shown in FIG. 10, the assembly 518 includes a safety cap 576 which is in the form of an end wall having a forwardly extending skirt. The pin 574 is integral with the central forward surface of the cap end wall and the skirt is recessed to engage over the exterior periphery of the rear end of the tubular housing member 522 and to provide a shoulder 578 to limit the forward movement of the cap 576 by engagement with the rear end wall 524.

The second releasing assembly 520 includes a manually engageable sleeve 580 slidably frictionally mounted over the exterior periphery of the outer housing member 522. Formed in the forward end of the sleeve 580 is a slot 582 which registers with a smaller slot 584 formed in the peripheral wall of the tubular housing member 522. A releasing lock or bolt 586 is slidably mounted in the slots 582 and 584 and has an angular slot 588 formed therein within which a pin 590 extends. Pin 590 is fixed to the portion of the sleeve 580 defining slot 582, as is best shown in FIG. 13. The bolt 586 in its locking or storage position, as shown in FIG. 10, extends into the interior of the housing member 522 and engages in front of an annular fitment 592 mounted forwardly of the outer container 546 at the position where it begins to neck down.

It will be understood that the apparatus 510 is assembled in much the same manner as a conventional single dosage automatic injector of the type disclosed in U.S. Pat. Nos. 3,882,863 and 4,031,893.

Figure 11:
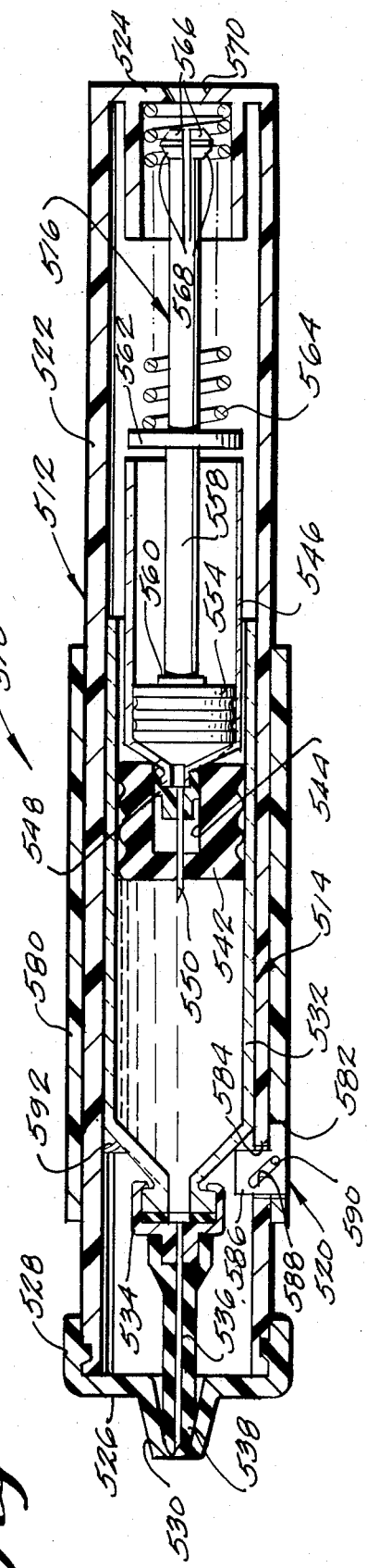
FIG. 11 is a view similar to FIG. 2 of the apparatus shown, in FIG. 10.

In operation, when it is desired to utilize the apparatus 510 the operator first removes the safety cap 576 which has the effect of withdrawing releasing pin 574. As previously indicated, the angular relationship between the plunger retaining surfaces 568 and 570 and the strength of spring 564 is such that movement of the plunger 558 commences in response to the withdrawal of the releasing pin 574. As soon as the releasing pin 574 is no longer in engagement with the plunger releasing surfaces 572, the spring fingers 566 of the plunger 558 are cammed radially inwardly so as to allow the plunger 558 to move forwardly. The forward movement of the plunger is transmitted through the forward end 560 to the piston 554 which, in turn, is transmitted through the liquid medicament 552 to the inner container 546. Consequently, during the initial movement of the plunger 558 following the first predetermined manual actuating procedure of removing the safety cap 576, the inner container 546 together with its hub assembly 548 and needle 550 is moved forwardly. On the other hand, forward movement of the piston 542 is resisted by virtue of the presence of the medicament ingredient 540 forwardly thereof and consequently the needle element 550 is pierced through the thin central portion of the piston 542 so as to communicate the interior of the inner container 546 with the interior of the outer container 532. As soon as this communication takes place the piston 542 and inner container member 546 are moved rearwardly as the liquid medicament ingredient 552 flows from the inner container into the outer container. Initially, blowout ring-shaped elements 556 are moved rearwardly out of sealing relation between the ends of the inner and outer containers, allowing further rearward movement of the piston 542 within the outer container 532 to be accomplished without an increase in the air pressure in the space rearwardly of the piston 542 between the interior of the outer container 532 and the exterior of the inner container 546. Because the pressure area of the piston 542 is greater than the pressure area of the piston 554 the flow of liquid from the inner container 546 into the outer container 532 will continue until such time as the piston 554 reaches the forward end of the inner container 546. This position is shown in FIG. 11 and it will be noted that the spring 564 has expanded axially only a small amount and hence considerable stress remains in the coil spring. This stress imposes a force upon the plunger 558 through the flange 562 which is transmitted through the piston 554, container 546, piston 542 and forwardly thereof to the outer container 532. The container 532 is prevented from moving forwardly under the bias of the initially released spring 564 due to the engagement of the locking bolt 586 with the fitment 592.

With the apparatus 510 in the position shown in FIG. 11, the operator can shake the unit to insure that the medicament ingredients are thoroughly mixed to form liquid medicament suitable to be injected. Injection is accomplished by the operator gripping the outer periphery of the sleeve 580 and moving the nose portion 530 into engagement with the skin of the patient in the area where the injection is to take place as, for example, the thigh. As the operator applies a forward force to the exterior of the sleeve 580 the pin 590 carried thereby is moved forwardly with respect to the outer housing member 522. This forward movement of the pin 590 by virtue of its engagement within the angular slot 588 causes the locking bolt 586 to move radially outwardly through the slots 584 and 582 into a position disposed out of engagement with the fitment 592 as shown in FIG. 12. This movement then constitutes the second predetermined manual actuating procedure which effects a second release of the stressed spring 564. This force which previously was acting upon the outer container 532 to move the same forward now causes this action to take place and the needle 536 moves outwardly of the resilient sheath 538 into the muscle tissue of the patient compressing the sheath until its compression retards or stops the forward movement of the outer container 532. Further movement under the bias of spring 564 results in the forward movement of the piston 542 within the outer container 532 until the piston reaches the forward end of the container discharging the last of the liquid medicament through the needle and into the muscle tissue of the patient. As before, the operation is completed by the operator simply moving the device rearwardly which causes the needle 536 to withdraw from the patient's muscle tissue.

In all of the embodiments of the present invention illustrated including the apparatus 10, the apparatus 210, the apparatus 410 and the apparatus 510, there is disclosed two separate medicament ingredients at least one of which is a liquid medicament ingredient. The other medicament ingredient is preferably in dry form, specifically a freeze dried powder, although it will be understood that the second liquid medicament may be in liquid form if desired. The liquid medicament which is formed in response to the first predetermined manual actuating procedure may be any desired liquid medicament. Examples are disclosed in my commonly assigned U.S. application Ser. No. 735,511 filed concurrently herewith.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. An automatic injecting apparatus comprising
an outer housing assembly including therein first and second medicament ingredient containers,
a hypodermic needle disposed within said outer housing assembly for movement from a storage position in a sterile condition outwardly of said outer housing assembly into the muscle tissue of a patient for passage of liquid medicament therethrough and into the muscle tissue of the patient,
a first liquid medicament ingredient in said first container,
a first piston mounted in said first container in a storage position in sealingly retaining relation with respect to said liquid medicament ingredient therein for movement from said storage postion relatively through said first container in a liquid medicament ingredient moving stroke,
a second medicament ingredient in said second container,
a second piston mounted in said second container for movement from a liquid medicament moving position through said second container in a liquid medicament discharging stroke,
spring means disposed within said outer housing assembly in a storage position in a releasable stressed condition capable of being released twice, first to move through a first piston moving stroke causing said first piston to move through its liquid medicament ingredient moving stroke and second to move through a second piston moving stroke causing said second piston to move through its liquid medicament discharging stroke,
first releasing means operable in response to a first predetermined manual actuating procedure for effecting the first release of the stressed condition of said spring means,
means operable when said first piston is moved through its liquid medicament ingredient moving stroke by the first release of the stressed condition of said spring means for causing the first liquid medicament ingredient discharging from said first container to flow into said second container to mix with the second medicament ingredient contained therein to form liquid medicament, and
second releasing means operable in response to a second predetermined manual actuating procedure for effecting the second release of the stressed condition of said spring means so as to cause said second piston to move through its liquid medicament discharging stroke during which said hypodermic needle is moved into the muscle tissue of the patient and the liquid medicament is moved through said needle into the muscle tissue of the patient.

2. An automatic injecting apparatus as defined in claim 1 including means for sealingly preventing flow of liquid outwardly of said needle while said needle is in its storage position operable after said needle is moved from said storage position to permit flow of liquid medicament outwardly of said needle, and second sealing means for preventing communication of said first liquid medicament ingredient with the second medicament ingredient in said second container operable in response to the release of the stressed condition of said spring means for permitting communication of the liquid medicament ingredient with the second medicament ingredient in said second container.

3. An automatic injecting apparatus as defined in claim 2 wherein said second piston is disposed in a storage position spaced from its liquid medicament moving position and is moved from its storage position into its liquid medicament moving position in response to the movement of the liquid medicament ingredient into said second container.

4. An automatic injecting apparatus as defined in claim 3 including means (1) for maintaining the space within said second container between the storage position of said second piston and the medicament moving position thereof in a sterile condition while said second piston is in said storage position and (2) for venting said space to atmosphere to allow movement of the second piston from said storage position into said liquid medicament moving position without air pressure build up capable of biasing said second piston away from said liquid medicament moving position toward said storage position after being moved into the liquid medicament moving position.

5. An automatic injecting apparatus as defined in claim 4 wherein said needle is mounted within said second container with the second medicament ingredient which is in dry form having a volume substantially less than the volume of said second container forwardly of said second piston when in its storage position, the aforesaid second container volume less the volume of said dry form medicament ingredient and said needle being filled with a gas, the gas within said second container being compressed during a first part of the liquid medicament discharging stroke of said second piston after which said needle is moved out of said second container into the muscle tissue of the patient and during the latter liquid medicament is moved out of the needle and into the muscle tissue of the patient.

6. An automatic injecting apparatus as defined in claim 5 including safety means (1) disposed in a safety position for rendering said first and second releasing means inoperable to release said spring means in response to said first and second actuating procedures respectively and (2) movable from said safety position for enabling said first and second releasing means to be operable to release said spring means in response to said first and second actuating procedures respectively.

7. An automatic injecting apparatus as defined in claim 6 wherein said spring means includes first and second stressed spring assemblies, each of said stressed spring assemblies comprising an elongated plunger having a plurality of annularly spaced elongated fingers connected with the rearward end of said plunger for radially inward movement from a plunger retaining position into a plunger releasing position, said fingers having exterior plunger retaining surfaces and interior plunger releasing surfaces, and a coil spring operatively connected with said plunger for movement from a storage position in a releasable stressed condition through a forward plunger moving stroke in response to the release of the stressed conditon thereof, each of said releasing means comprising a releasing pin (1) disposed in a storage position in engagement with the associated interior plunger retaining surfaces in radially inward movement preventing relation with respect to the associated fingers and (2) operable in response to movement out of said storage position to permit radially inward movement of the associated fingers, and cooperating plunger retaining surface means engaging the exterior plunger retaining surfaces associated with each plunger for (1) retaining (a) the associated plunger against forward movement and (b) the associated spring in stressed condition when the associated releasable pin is in said storage position and (2) for enabling the stressed condition of the associated spring to effect (a) radially inward movement of the associated fingers and (b) forward movement of the associated plunger in response to the movement of the associated releasing pin out of said storage position and the movement of the associated spring through said forward plunger moving stroke.

8. An automatic injecting apparatus as defined in claim 7 wherein said second releasing pin includes a movement preventing portion disposed in engagement with the associated interior plunger retaining surfaces when said second releasing pin is in said storage position, an actuating button spaced rearwardly from said movement preventing portion and movable forwardly to move the latter out of its storage position and a movement enabling portion fixed between said movement preventing portion and said actuating button for permitting radially inward movement of the associated fingers when said actuating button is moved forwardly.

9. An automatic injecting apparatus as defined in claim 8 wherein said safety means includes a safety cap having a rear wall and a forwardly extending skirt, means mounting said safety cap on said outer housing assembly for movement by a manual push while gripping said skirt from a safety position wherein said rear wall is rearwardly of said actuating button into a forward actuating positiion wherein said actuating button is moved forwardly, and a safety key member removably mounted from a safety position preventing movement of said safety cap forwardly from its safety position, said safety key being fixed to said first releasing pin, said first predetermined actuating procedure comprising removing said safety key, said second predetermined actuating procedure comprising manually pushing said skirt while gripping the same.

10. An automatic injecting apparatus as defined in claim 5 wherein said first and second containers are formed by a single outer housing member having first and second parallel cylindrical and second (1) medicament ingredients are contained and (2) pistons are slidably sealingly mounted.

11. An automatic injecting apparatus as defined in claim 10 wherein said means for causing said first liquid medicament ingredient to flow into said second container comprises a passage in said single housing member between said first and second cavities, said second sealing means comprising a piston valve disposed in a storage position within said first cavity in sealing relation between the first liquid medicament ingredient and said passage and movable forwardly from said storage position to communicate the first liquid medicament ingredient with said passage.

12. An automatic injecting apparatus as defined in claim 11 wherein said needle flow preventing means comprises a forward stopper in the forward end of said second container through which said needle extends during its movement out of its storage position into the muscle tissue of the patient.

13. An automatic injecting apparatus as defined in claim 10 wherein said means for causing said first liquid medicament ingredient to flow into said second container comprises a passage in said single housing member between said first and second cavities, and a piston valve disposed in a storage position within said first cavity in sealing relation between the first liquid medicament ingredient and said passage operable in response to ingredient and said passage operable in response to the first release of the stressed condition of said spring to move forwardly from said storage position to communicate the first liquid medicament ingredient with said passage.

14. An automatic injecting apparatus as defined in claim 2 wherein said needle flow preventing means comprises a resilient sheath receiving a sharpened end portion of the needle in sealing relation and covering the exterior thereof, said resilient sheath being operable during the movement of the needle out of its storage position to permit the sharpened end portion of said needle to penetrate through said resilient sheath and to thereafter be compressed against said outer housing assembly to resiliently arrest the movement of said needle outwardly of said outer housing assembly and into the muscle tissue of the patient.

15. An automatic injecting apparatus as defined in claim 2 wherein said needle flow preventing means comprises a forward stopper in the forward end of said second container through which said needle extends during its movement out of its storage position into the muscle tissue of the patient.

16. An automatic injecting apparatus as defined in claim 1 wherein said spring means includes separate first and second stressed spring assemblies separately movable through said first and second piston moving strokes respectively.

17. An automatic injecting apparatus as defined in claim 16 wherein said needle is fixedly connected with rigid inner housing structure mounted in said outer housing assembly for movement from a storage position within said outer housing assembly into an injecting position within said outer housing assembly.

18. An automatic injecting apparatus as defined in claim 17 wherein said first spring assembly is operatively conected between said inner housing structure and said first piston.

19. An automatic injecting apparatus as defined in claim 18 including means for (1) fixedly securing said first and second containers together and (2) fixedly securing said first and second containers to said inner housing structure 20. An automatic injecting apparatus as defined in claim 17 including means for (1) fixedly securing said first and second containers together and (2) securing said first and second containers for movement together with respect to said inner housing structure from a storage position into a mixing position wherein both of said containers are thereafter movable with said inner housing structure.

21. An automatic injecting apparatus as defined in claim 20 wherein each of said containers includes forward ends having rupturable diaphragms sealingly covering the same when said containers are in said storage position, and means for rupturing said diaphragms in response to the movement of said containers together from said storage position into said mixing position.

22. An automatic injecting apparatus as defined in claim 1 wherein said spring means includes a single stressed spring assembly movable sequentially through said first and second piston moving strokes.

23. An automatic injecting apparatus as defined in claim 1 wherein said first container is arranged in telescoping relation within said second container within said outer housing assembly when in a storage position.

24. An automatic injecting apparatus as defined in claim 20 wherein said first container is fixed at its forward end with said second piston.

25. An automatic injecting apparatus as defined in claim 1 including safety means (1) disposed in a safety position for rendering said first and second releasing means inoperable to release said spring means in response to said first and second actuating procedures respectively and (2) movable from said safety position for enabling said first and second releasing means to be operable to release said spring means in response to said first and second actuating procedures respectively.

26. An automatic injecting apparatus as defined in claim 25 wherein said spring means includes first and second stressed spring assemblies, each of said stressed spring assemblies comprising an elongated plunger having a plurality of annularly spaced elongated fingers connected with the rearward end of said plunger for radially inward movement from a plunger retaining position into a plunger releasing position, said fingers having exterior plunger retaining surfaces and interior plunger releasing surfaces, and a coil spring operatively connected with said plunger for movement from a storage position in a releasable stressed condition through a forward plunger moving stroke in response to the release of the stressed condition thereof, each of said releasing means comprising a releasing pin (1) disposed in a storage position in engagement with the associated interior plunger retaining surfaces in radially inward movement preventing relation with respect to the associated fingers and (2) operable in response to movement out of said storage position to permit radially inward movement of the associated fingers, and cooperating plunger retaining surface means engaging the exterior plunger retaining surfaces associated with each plunger for (1) retaining (a) the associated plunger against forward movement and (b) the associated spring in stressed condition when the associated releasable pin is in said storage position and (2) for enabling the stressed condition of the associated spring to effect (a) radially inward movement of the associated fingers and (b) forward movement of the associated plunger in response to the movement of the associated releasing pin out of said storage position and the movement of the associated spring through said forward plunger moving stroke.

27. An automatic injecting apparatus as defined in claim 26 wherein said second releasing pin includes a movement preventing portion disposed in engagement with the associated interior plunger retaining surfaces when said second said releasing pin is in said storage position, an actuating button spaced rearwardly from said movement preventing portion and movable forwardly to move the latter out of its storage position and a movement enabling portion fixed between said movement preventing portion and said actuating button for permitting radially inward movement of the associated fingers when said actuating button is moved forwardly.

28. An automatic injecting apparatus as defined in claim 27 wherein said safety means includes a removable safety cap mounted on said outer assembly housing in covering relation with respect to said actuating button and in fixed relation to said first releasing pin, said first predetermined manual actuating procedure comprising removing said safety cap, said second predetermined actuating procedure comprising pushing said actuating button forwardly.

29. An automatic injecting apparatus as defined in claim 28 wherein said safety means includes a safety cap having a rear wall and a forwardly extending skirt, means mounting said safety cap on said outer housing assembly for movement by a manual push while gripping said skirt from a safety position wherein said rear wall is rearwardly of said actuating button into a forward actuating position wherein said actuating button is moved forwardly, and a safety key member removably mounted from a safety position preventing movement of said safety cap forwardly from its safety position, said safety key being fixed to said first releasing pin, said first predetermined actuating procedure comprising removing said safety key, said second predetermined actuating procedure comprising manually pushing said skirt while gripping the same.

30. An automatic injecting apparatus as defined in claim 1 wherein said second piston is disposed in a storage position spaced from its liquid medicament moving position and is moved from its storage position into its liquid medicament moving position in response to the movement of the liquid medicament ingredient into said second container.

31. An automatic injecting apparatus as defined in claim 30 including means (1) for maintaining the space within said second container between the storage position of said second piston and the medicament moving position thereof in a sterile condition while said second piston is in said storage position and (2) for venting said space to atmosphere to allow movement of the second piston from said storage position into said liquid medicament moving position without air pressure build up capable of biasing said second position toward said storage position after being moved into the liquid medicament moving position.

32. An automatic injecting apparatus as defined in claim 30 wherein said needle is mounted within said second container with the second medicament ingredient which is in dry form having a volume substantially less than the volume of said second container forwardly of said second piston when in its storage position, the aforesaid second container volume less the volume of said dry form medicament ingredient and said needle being filled with a gas, the gas within said second container being compressed during a first part of the liquid medicament discharging stroke of said second piston after which said needle is moved out of said second container into the muscle tissue of the patient and during the latter liquid medicament is moved out of the needle and into the muscle tissue of the patient.

33. An automatic injecting apparatus as defined in claim 32 wherein said first and second containers are formed by a single outer housing member having first and second parallel cylindrical cavities therein within which the respective first and second (1) medicament ingredients are contained and (2) pistons are slidably sealingly mounted.

34. An automatic injecting apparatus as defined in claim 1 wherein said medicament ingredient within said second container is in a dry form and said liquid medicament ingredient is a diluent for said dry form medicament ingredient.

* * * * *